United States Patent
Leonard et al.

(10) Patent No.: US 11,083,601 B1
(45) Date of Patent: Aug. 10, 2021

(54) PROSTHETIC HAND SYSTEM

(71) Applicants: Braden William Thomas Leonard, Newport, RI (US); Manuel Reyes, Newport, RI (US); David Thomas Moy, Jr., Wellesley, MA (US)

(72) Inventors: Braden William Thomas Leonard, Newport, RI (US); Manuel Reyes, Newport, RI (US); David Thomas Moy, Jr., Wellesley, MA (US)

( * ) Notice: Subject to any disclaimer, the term of this patent is extended or adjusted under 35 U.S.C. 154(b) by 0 days.

(21) Appl. No.: 16/029,925

(22) Filed: Jul. 9, 2018

Related U.S. Application Data (60) Provisional application No. 62/530,334, filed on Jul. 10, 2017.

(51) Int. Cl.
| | | |
|---|---|---|
| *A61F 2/58* | (2006.01) | |
| *A61F 2/78* | (2006.01) | |
| *B62J 99/00* | (2020.01) | |
| *A61F 2/50* | (2006.01) | |
| *B62J 11/20* | (2020.01) | |
| *A61F 2/54* | (2006.01) | |
| *A61F 2/76* | (2006.01) | |

(52) U.S. Cl.
CPC .............. *A61F 2/588* (2013.01); *A61F 2/585* (2013.01); *A61F 2/78* (2013.01); *B62J 99/00* (2013.01); *A61F 2/76* (2013.01); *A61F 2002/5067* (2013.01); *A61F 2002/5072* (2013.01); *A61F 2002/543* (2013.01); *A61F 2002/7875* (2013.01); *B62J 11/20* (2020.02)

(58) Field of Classification Search
CPC ........ A61F 2/50; A61F 2/5081; A61F 2/5083; A61F 2/54; A61F 2/583; A61F 2/585; A61F 2/588; A61F 2/76; A61F 2/78; A61F 2002/543; A61F 2002/7875; A61F 2002/7887
See application file for complete search history.

(56) References Cited

U.S. PATENT DOCUMENTS

| | | | |
|---|---|---|---|
| 8,246,693 B2 * | 8/2012 | Bachus | A61F 2/2814 623/32 |
| 9,408,723 B2 * | 8/2016 | Branemark | A61F 2/78 |
| 2008/0288087 A1 * | 11/2008 | Bachus | A61F 2/2814 623/34 |
| 2015/0257904 A1 * | 9/2015 | Branemark | A61F 2/78 623/32 |
| 2018/0325701 A1 * | 11/2018 | Ortiz Catalan | A61F 2/68 |

* cited by examiner

*Primary Examiner* — Marcia L Watkins
(74) *Attorney, Agent, or Firm* — Keeley DeAngelo LLP; W. Scott Keeley (57) ABSTRACT

A prosthetic system and terminal device for gripping and maneuvering handlebars. The prosthetic hand engages a handlebar throughout the necessary range of motion required for balance, steering and pulling, while allowing release in an atypical motion, allowing the wearer to disengage from the handlebar, particularly in the event of a fall.

3 Claims, 11 Drawing Sheets

PROSTHETIC HAND SYSTEM

TECHNICAL FIELD

The present disclosure relates to prosthetic devices in general and to upper limb terminal devices used for gripping and maneuvering handlebars.

BACKGROUND

A prosthesis is any artificial device that replaces a body part, There are a number of important design considerations and aspects of prosthetic design. The fit of a prosthetic device accommodates the nature of the activity, the level of muscle strain, and user perspiration, Energy storage and return is a design consideration that affects the impact on the device and the response from the device to the impact. Utility, weight, and durability of the components affects the comfort and performance of a prosthesis.

A prosthetic socket is the customized biological interface suspended to a residual limb of an amputee. Prosthetic sockets are typically semi-rigid composite forms constructed with a number of components engaged along a central axis. These integrated components often include suspension methods, elbow, wrist, knee, and ankle units, and use-specific terminal devices.

Suspension refers to the interaction between the prosthetic socket and device and the body. There are various methods to suspend a prosthetic device from the body. There are proximal (above the amputation) and distal (below the amputation) means of suspension.

An epicondyle is a protuberance above or on the condyle of a long bone, especially either of the two at the elbow end of the humerus. An olecranon is the bony prominence of the elbow, on the upper end of the ulna.

Pronation and supination describe the rotation of the forearm to move the hand into a palm-up (pronation) or palm-down (supination) position. Internal and external rotation is the rotation of the arm at the shoulder or leg at the pelvis. Internal and external rotation at these joints rotates all of the distal extremities relative to the torso. Pronation, supination and internal and external rotation, whether intentional or unintentional, are important design consideration for prosthetic devices.

A mechanical wrist unit is one of the distal components of an upper limb prosthetic socket. The wrist unit allows for secure attachment, removal, and rapid re-attachment of various terminal devices. The wrist unit design facilitates free rotation and angular positioning of the terminal device.

A terminal device is a prosthetic device that allows the user to perform various specialized tasks. The terminal device attaches to a mechanical wrist unit. The terminal device typically has a threaded stud, which threads into an adapter. The adapter is dependent on the design of the wrist unit.

Handlebars are used for steering various motor- and human-powered vehicles. For the purpose of clarity, handlebars for bicycles are described herein. Handlebars are designed with the specific dynamics of the type of riding and terrain. Racing bicycles, for example, are designed to allow the rider to remain in an aerodynamic position while pedaling. Mountain bicycles have longer handlebars for greater stability. Although handlebars' primary purpose is steering, a cyclist may use handlebars to create opposing force, pulling up on them while pushing down with their feet on the pedals. Increased force is used in hill-climbing or to move through rough terrain.

Clips and cleats are common add-ons to bicycle pedals. They create a firm connection between a cyclist's feet and the bicycle's pedals, increasing the efficiency of the transfer of energy between the cyclist's leg force and the drive force applied to the rear wheel.

Cleats involve a combination of a specially configured shoes and pedals. A cleat is a piece of metal or plastic hardware affixed to the bottom of a shoe that mates with a receiving pedal. A cleat engages a cyclist's foot with a pedal throughout the range of useful motion while allowing release in an alternate motion. Typically the cleat is disengaged by twisting outward. The intent of the design is to allow for ease of removal when stopping or in the event of a fall. In other words, a cleat offers substantially firm engagement without sacrificing the ease of removal. A cyclist's legs do not commonly remain in a single plane while pedaling. The term "float" refers to the degree of movement, or twist, offered by a cleat without detaching. The term "tension" refers to the amount of resistance to the degree of movement, or float, that a cleat exerts.

It can be seen that the useful features that apply a firm engagement between a shoe and a pedal, while allowing release in an alternate motion, may be applied to a prosthesis and handlebar of a bicycle or other handlebar-operated vehicle.

SUMMARY

In accordance with example embodiments of the present disclosure, a method, system, and apparatus of components within a prosthetic hand is described. The invention includes a prosthetic terminal device for gripping handlebars.

In one embodiment a prosthetic socket is connected with a person's arm by way of a flexible fabric cuff placed on the upper arm. This cuff is joined by adjustable straps or a hinge to the socket on the forearm of the user. The flexible fabric cuff is constructed of opposing-direction, radial, braided material. The invention includes a material with 0%-1% longitudinal stretch and 15%-25% circumferential stretch. In other words, the flexible fabric cuff flexes between 0% and 1% in a direction parallel to the limb and between 15% and 25% about the circumference of the limb. One skilled in the art is familiar with opposing-direction radial braided systems that tighten on a cylindrical form when pulled. The semi-rigid form has a mechanical connection to the socket.

In one embodiment the prosthetic socket is connected with the arm by way of a semi-rigid composite cuff on the upper arm. This cuff is joined by a reverse-purchase rigging system to the socket. The semi-rigid cuff is cushioned with a structural composite batten within the cuff. Distal tension engages the reverse-purchase system which results in circumferential closing of the cuff over the upper limb. In other words, the cuff engages with increased circumferential tension with increased pull in a direction parallel to a central axis of the limb. One unit of movement in the direction parallel to the central axis of the limb results in 5 units of circumferential closure around the limb. One unit of force pull results in 0.2 units of circumferential closure force around the limb. The cuff engages the epicondyles and olecranons in the elbow to suspend the prosthetic socket from the arm, and prevent unintentional doffing of the prosthesis.

The residual limb is connected distally to the prosthetic socket using a liner and locking method. A composite liner made of silicone and fabric covers the residual limb. The distal end of the liner has hardware which interfaces with a locking device inside the prosthetic socket distally suspending the socket to the limb using friction within the liner. In this embodiment, the liner and lock are designed such that rotation of the forearm about the radius and ulna bones rotates the hand prosthesis. Components are configured to provide secure engagement with rotational interference such that rotation of the forearm translates to rotation of the hand prosthesis with minimal rotational slippage between components. The central axis of the hand prosthesis and the central axis of the user's forearm remain substantially collinear. The single central axis is replaced by two axes to simulate the movement of the radius and ulna so as to transfer pronation and supination.

Integrated within the prosthetic socket is a mechanical wrist unit designed for full, free rotation under all load cases. A combination thrust bearing and tapered bearing allow for free rotation as desired, with locking positions for the prosthesis while under axial load. The wrist unit is connected to the terminal device using an adapter. Distally, it has a T-hook and is inserted into a keyhole in the wrist unit and turned 90 degrees for the T-hook to seat in a locked position. It is held in the locked position mechanically using a threaded collet thus locking the T-hook into the seat within the wrist unit.

An example embodiment of the present disclosure is a prosthetic terminal device that engages a handlebar through the necessary range of motion required for balance, steering and pulling while allowing release in a non-typical motion, allowing the user to disengage from the handlebar, particularly in the event of a fall. A series of internal components provide for float and tension in the terminal device.

Components of a prosthesis that require flexible engagement between, for example, a cuff and a socket, may be connected by way of straps and pronged clips. In some embodiments a pronged clip is provided that may be engaged with one hand only.

One skilled in the art understands that many vehicles are controlled by handlebars, including motorcycles, mopeds, motor scooters, and the like. The present disclosure describes the invention in relation to bicycle handlebars.

Other objects and features will become apparent from the following detailed description considered in conjunction with the accompanying drawings. Drawings are designed to illustrate rather than define the limits of the invention.

BRIEF DESCRIPTION OF THE DRAWINGS

To assist those of skill in the art in making and using the disclosed prosthesis and associated methods, reference is made to the accompanying figures, wherein.

DESCRIPTION

Figure 1:
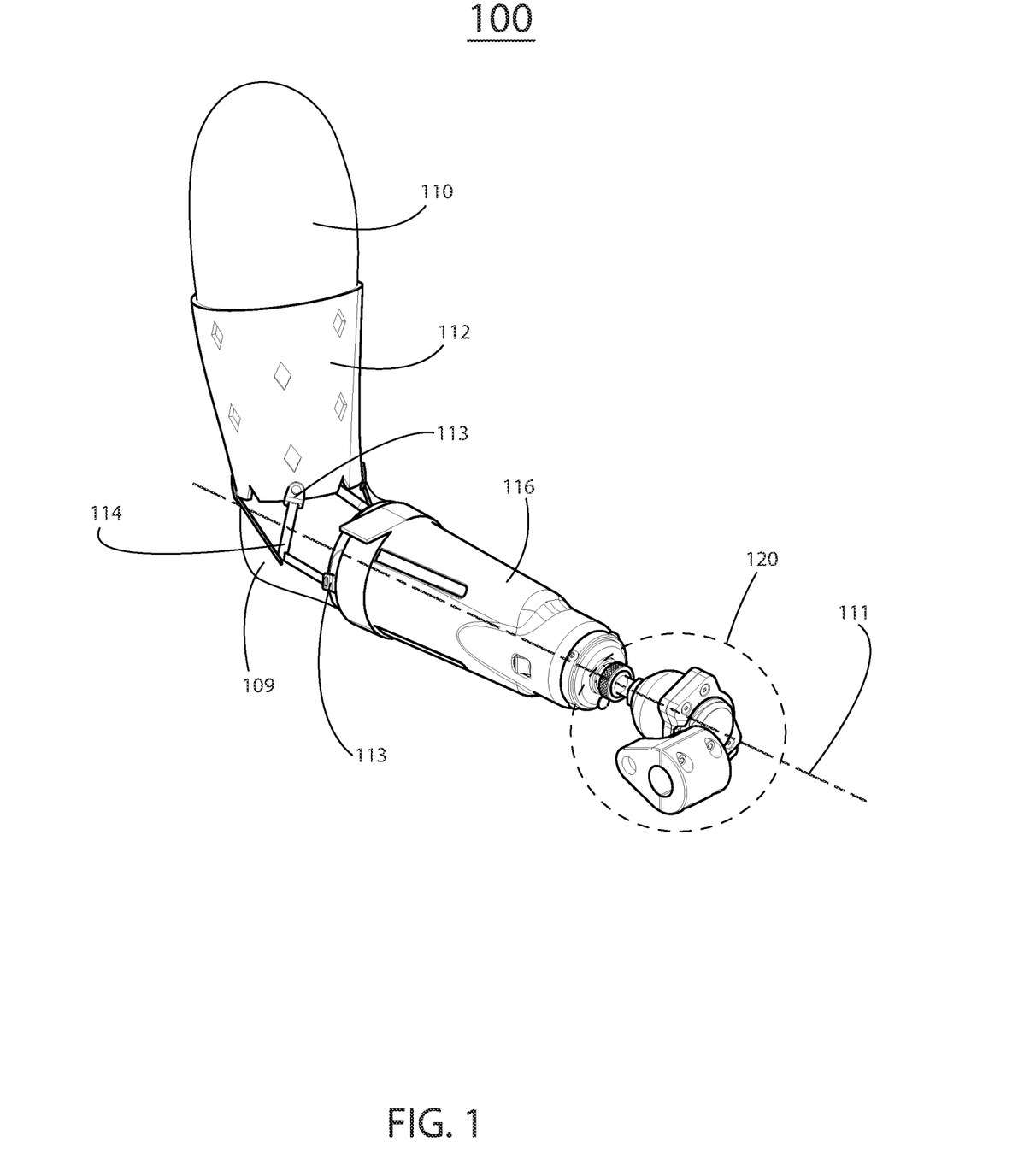
FIG. 1 is a perspective view of an example embodiment as worn on the arm.

Referring to FIG. 1, a prosthesis for engaging an arm 110 with a handlebar is shown. A cuff 112 is made of opposing direction helically woven material such that pulling against the lower edge of the cuff causes the woven material to tighten about the upper arm 110. Straps 114 connect the cuff with a socket 116. The socket 116 is affixed to the lower arm 109. The socket 116 is coaxial with the forearm 109 about an axis 111. A wrist unit and terminal device 120 is affixed to the socket 116.

Figure 2:
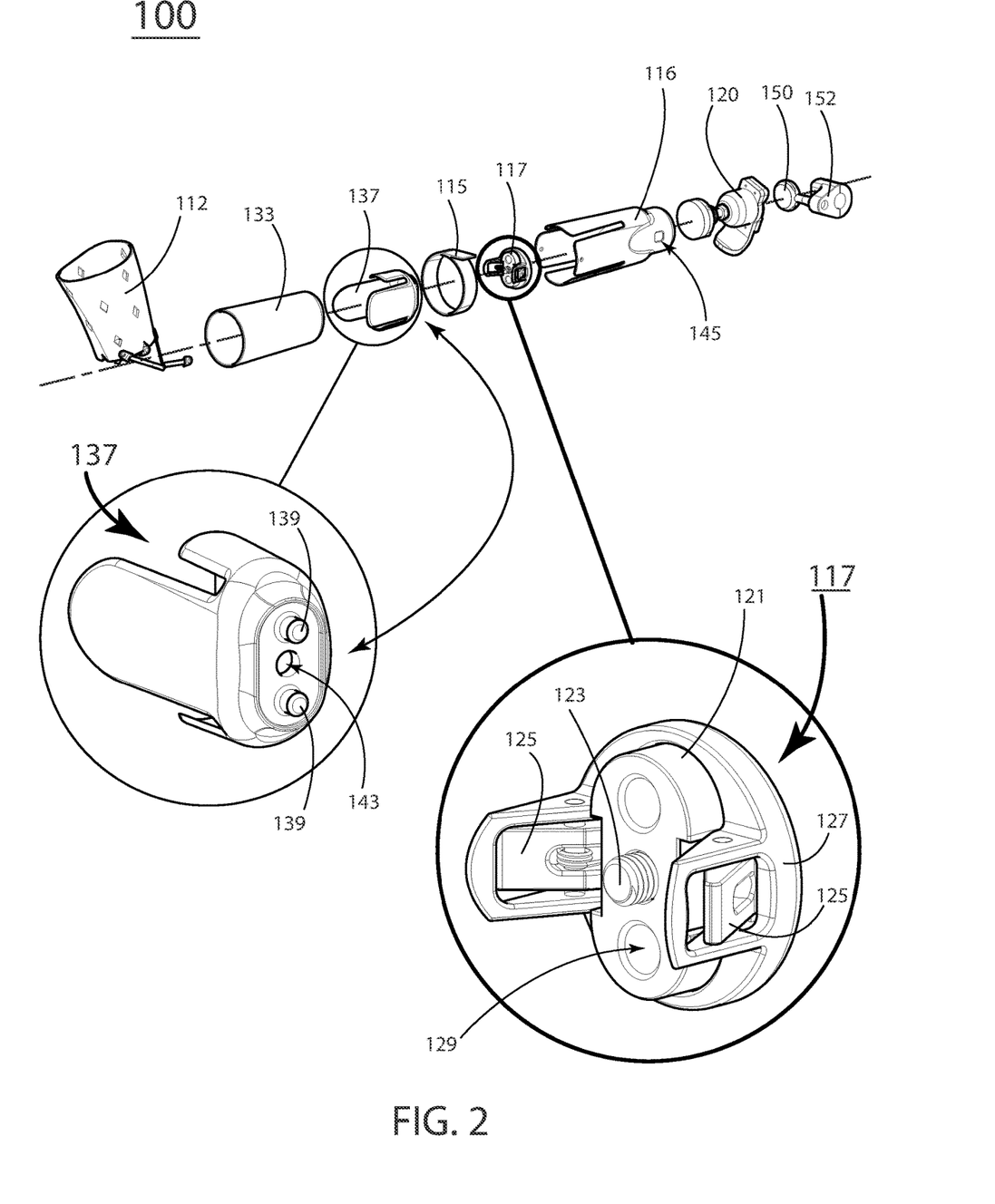
FIG. 2 is an exploded view of the example embodiment of FIG. 1 with a detail view depicting a rotational locking device.

FIG. 2 shows an exploded view of the apparatus of FIG. 1 and a detailed view of a rotational interference device 117 that mates with a sleeve 137. The sleeve is shown in both exploded view and detailed view. The sleeve 137 has been rotated approximately 90° to show the engagement with the rotational interference device 117. The sleeve fits inside the socket lining 133. The socket lining is cylindrical and is open on both ends, allowing the sleeve 137 to extend through and engage with the rotational interference device 117. From the detailed views it can be seen that protrusions 139 engage with holes 129 and protrusion 123 engages with hole 143. One skilled in the art can understand that various combinations of shapes and detents can be used to engage a form such as the sleeve 137 with a rotational interference device 117. The socket is engaged with a strap 115 that assists in reducing the diameter of the socket 116 to form a snug fit over the forearm. The socket 116 is further engaged with the wrist unit and terminal device 120 which is in turn engaged with the receiving member 150 and handlebar bracket 152 assembly.

The rotational interference device 117 engages with the interior of the socket 116 and is firmly engaged by way of spring loaded tabs 125 that spring into receiving holes 145. The rotational interference device 117 has a housing 127 that supports the non-round engagement portion 121 that has holes 129 and at least one protrusion 123 for engaging with the corresponding protrusions 139 and at least one hole 143 on the sleeve 137. The housing 127 also supports the spring loaded tabs 125 that engage with the receiving holes 125 in the socket 116.

Figure 3:
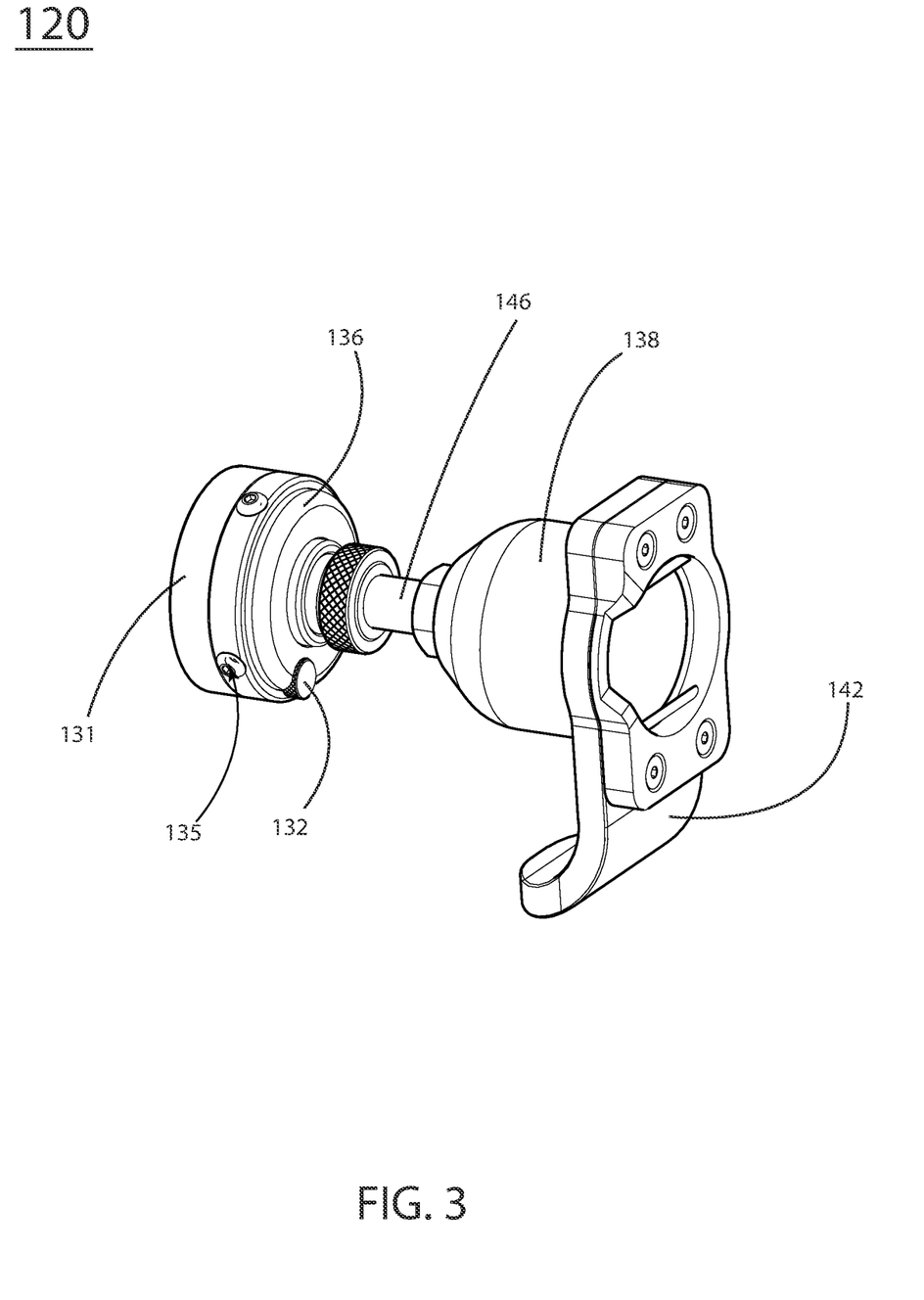
FIG. 3 is a perspective view depicting the wrist unit and terminal device of the embodiment of FIG. 1.

Referring to FIG. 3 a combination wrist unit and terminal device is shown. A wrist unit has a locking gear housing 131, for containing a locking gear 130 (FIG. 4) and a series of holes for fasteners 135 (FIG. 3). A locking plunger 132 may be disengaged to allow for rotation of the cleat to a rotational position preferred by the user and then re-engaged to lock the rotational position. The terminal device is made up of a spherical eye-stud 146 that is engaged with a cleat 142 and has a motion damper 138. The terminal device is more completely described in FIG. 5.

Figure 4:
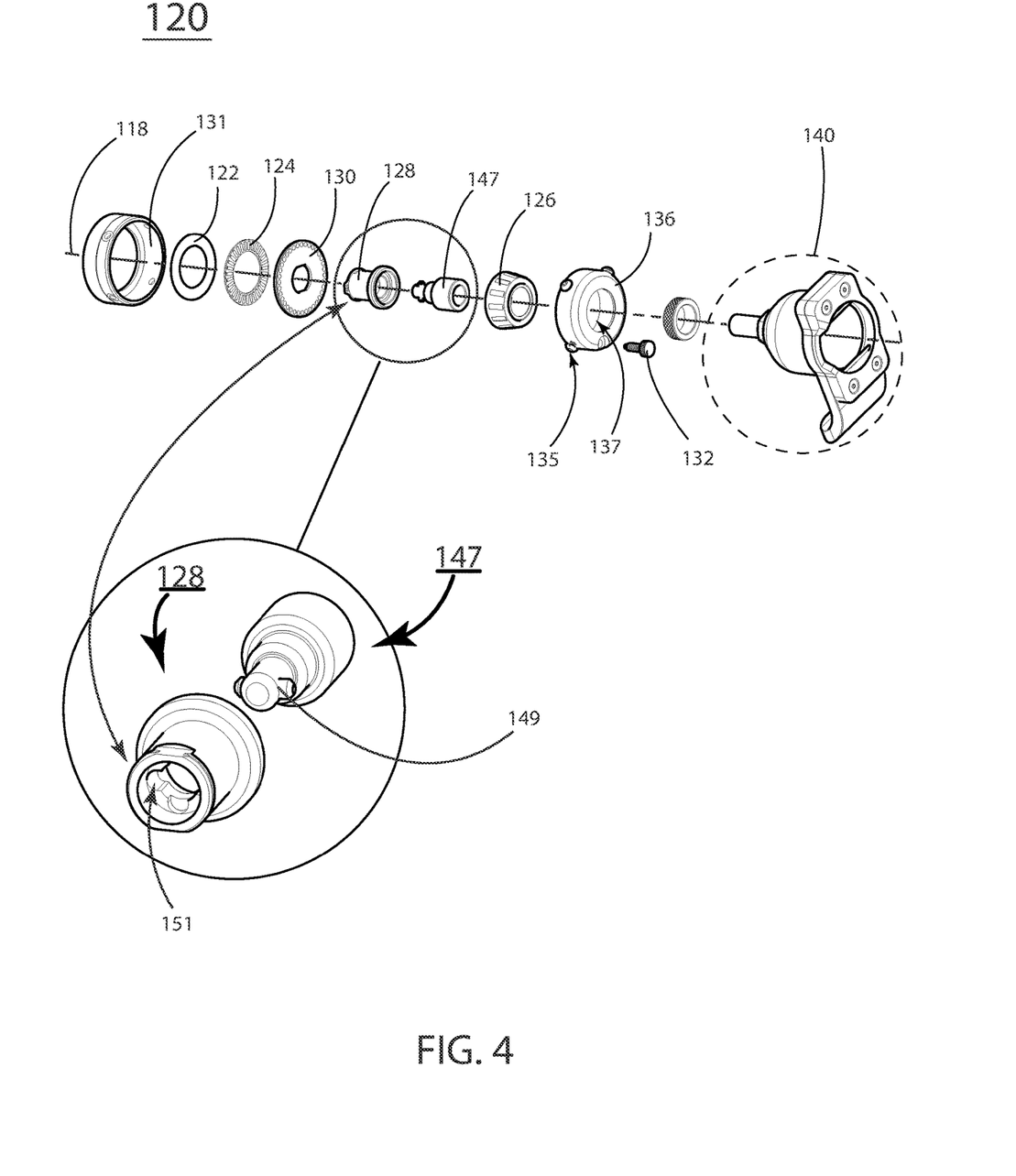
FIG. 4 is a perspective, exploded view of a wrist unit and terminal device of the embodiment of FIG. 3.

FIG. 4 shows an exploded view of the wrist unit and a terminal device. The majority of the components are exploded along an axis 118. A needle-bearing washer 122 provides a base for the needle bearing 124 to roll on. A thrust bearing 126 is in rotational contact with the needle bearing 124. Together the needle bearing 124 and thrust bearing 126 allow for rotation of the gear 130 and the spindle 128 while the housing base 131 is under axial load along axle 118. An adapter 147 is engaged with the terminal device 140. The adapter 147 fits inside the inner diameter of the spindle 128. The spindle 128 is interference-fit into the thrust bearing 126, with flats engaging the gear 130. The spindle 128 and gear 130 combination can be locked using the locking pin 132. While in the locked position, the spindle 128, gear 130, adapter 147, and terminal device 140 assembly are prevented from spinning. (FIG. 5) The detail view in FIG. 4 illustrates the fit between the adapter 147 and receptacle 151. The view is rotated 90° to show the manner in which the adapter 147 fits into the receptacle 151. One skilled in the art understands that a cross-pin 149 in a cylinder mating with a cross-wise hole 151 will prevent rotational motion between a shaft and a cylindrical receptacle, while retaining the adapter 147.

Referring again to FIG. 4, the spindle 128 is engaging a locking gear 130 that is an annular array of gear teeth. One skilled in the art understands that a gear may have various embodiments of gear teeth including those as depicted in FIG. 13. The gear 130 receives a locking pin 132 for indexing and locking the housing 131 at a desired rotational angle as chosen by the user. A key 144 affixes the spherical eye-stud 146 (FIG. 5) to the housing 131. Referring back to FIG. 4, a housing cover 136 fits over the housing 131 and is affixed to the housing by fasteners that fit through holes 135 and engage with the housing 131. The bicycle terminal device 140 is engaged with the adapter 147 along the axis 118. A more detailed description of the terminal device is shown in FIG. 5.

Figure 5:
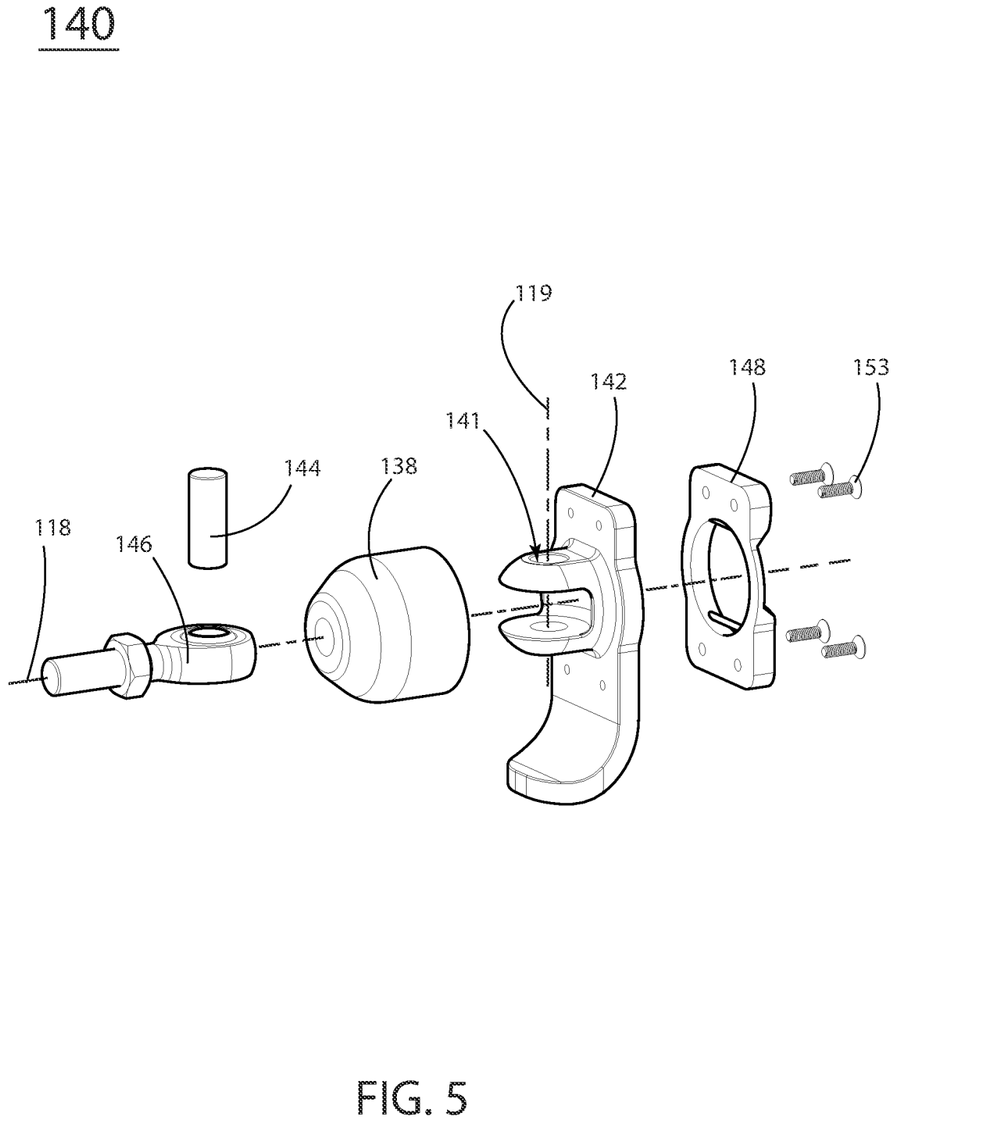
FIG. 5 is an exploded view of the terminal device of FIG. 4.

Referring to FIG. 5, an exploded view of the bicycle terminal device 140 is depicted in the illustration. The terminal device is configured to provide float and tension in the connection with the bicycle. A spherical eye-stud is engaged with a cleat 142 by way of a spherical eye-stud shaft 144 that is press-fit into a hole 141 in the cleat 142. The spherical eye-stud shaft allows for rotation about a vertical axis 119. A motion damper 138 is affixed over the spherical eye-stud and cleat assembly to dampen movement of the spherical eye-stud with respect to the cleat 142. The spherical eye-stud 146 is allowed to float about the central axis 118 and a vertical axis 119. The movement damper 138 is affixed to the spherical eye-stud and to the cleat 142 and thus provides tension, otherwise referred to as damping, to the float motion. Fasteners 153 affix the engagement 148 to the cleat 142. The engagement 148 is configured to engage with a receiving member 150 (FIG. 7) and may be exchanged for other engagements as receiving members are changed.

Figure 6:
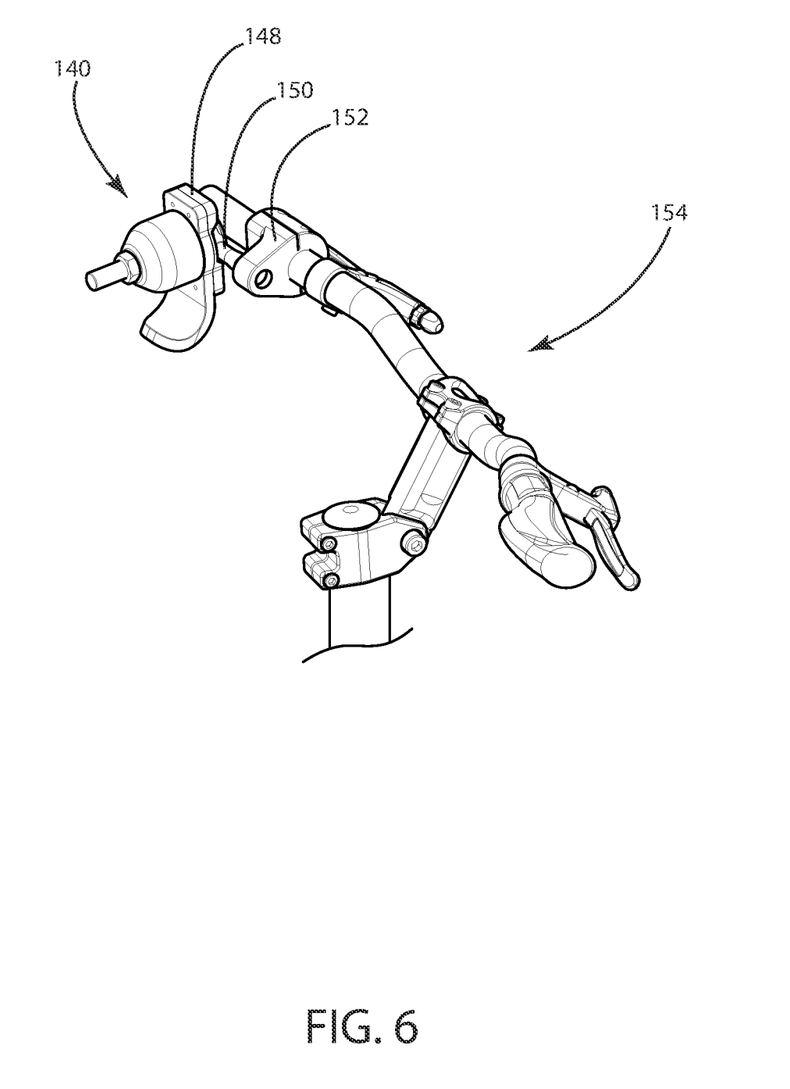
FIG. 6 is a perspective view of the terminal device of FIG. 3 and FIG. 4, as mounted on a bicycle handlebar.
Figure 7:
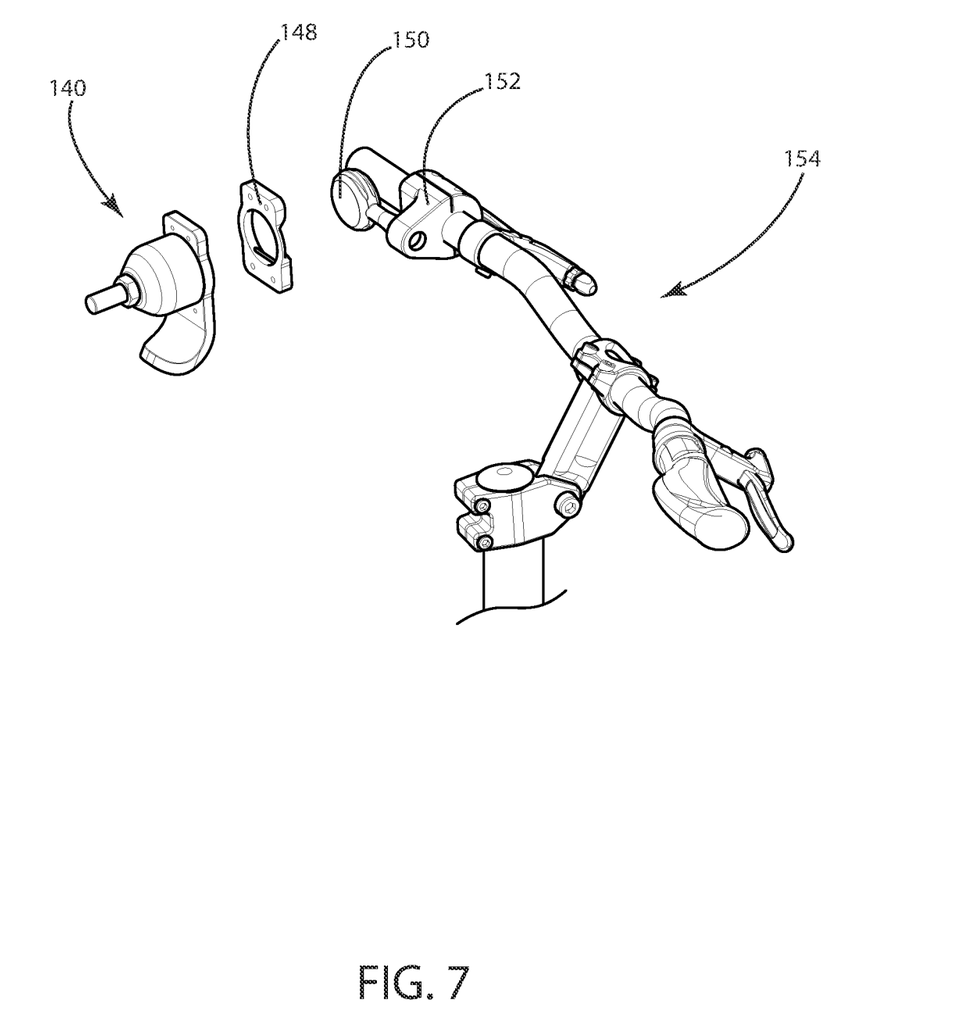
FIG. 7 is a perspective, exploded view of the terminal device of FIG. 3 and FIG. 4, as mounted on a bicycle handlebar.

FIGS. 6 and 7 show a perspective view of the terminal device 140 as engaged with a common handlebar assembly 154 in both assembled view (FIG. 6) and exploded view (FIG. 7). A handlebar bracket 152 clamps onto a handlebar assembly 154 in the region where one would likely grip the handlebar. A receiving member 150 receives a clip-engagement member 148. The clip-engagement member 148 is affixed to the bicycle terminal device 140. The clip-engagement member 148 is configured to engage with the receiving member 150. One skilled in the art understands that a change in the design of a receiving member 150 may include a change in the design of the clip-engagement member 148. The new clip-engagement member may then be affixed to the terminal device 140 without the need to re-design the terminal device 140.

Figure 8:
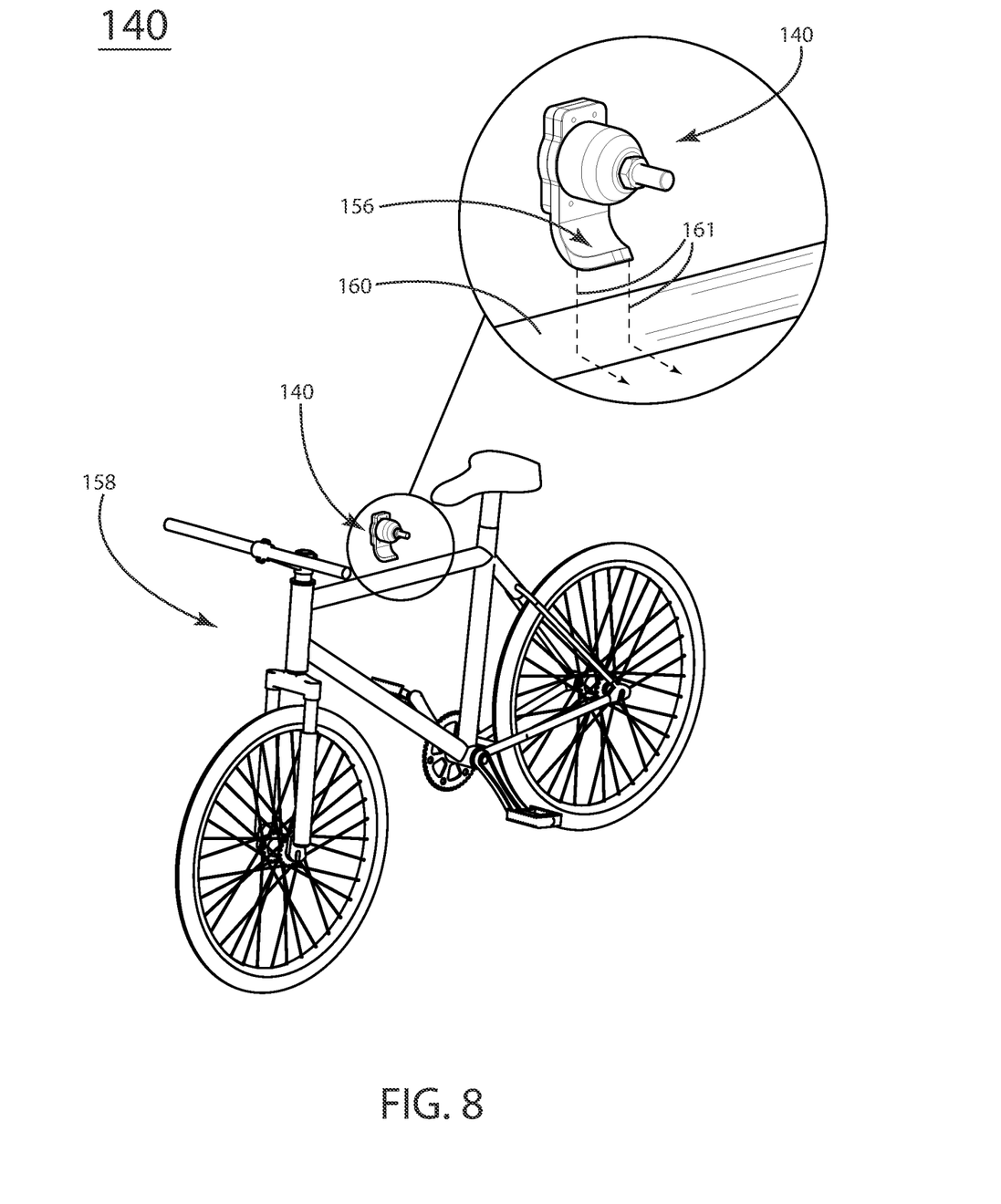
FIG. 8 is a perspective view of the terminal device of FIG. 3 and FIG. 4, depicting a carrying loop feature of the terminal device.
Figure 9:
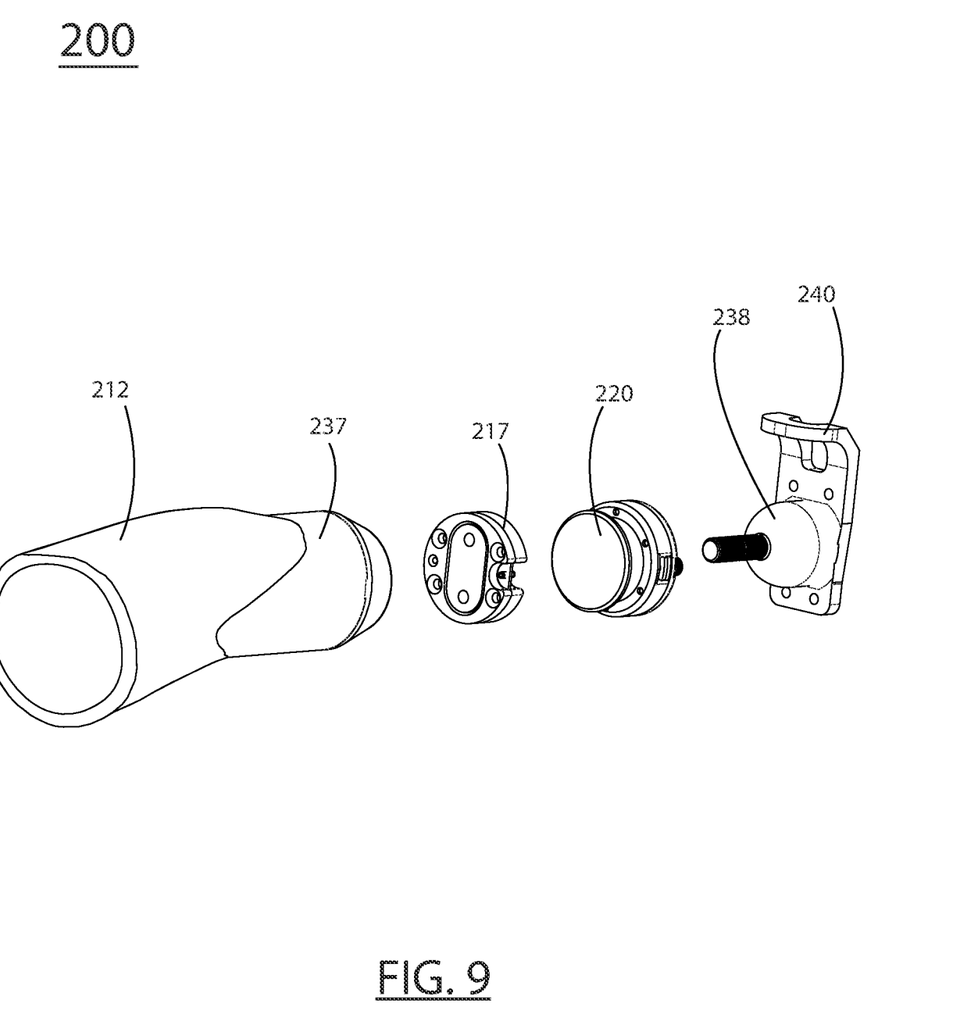
FIG. 9 is a perspective, partially exploded, view of an iteration of the embodiment.
Figure 10:
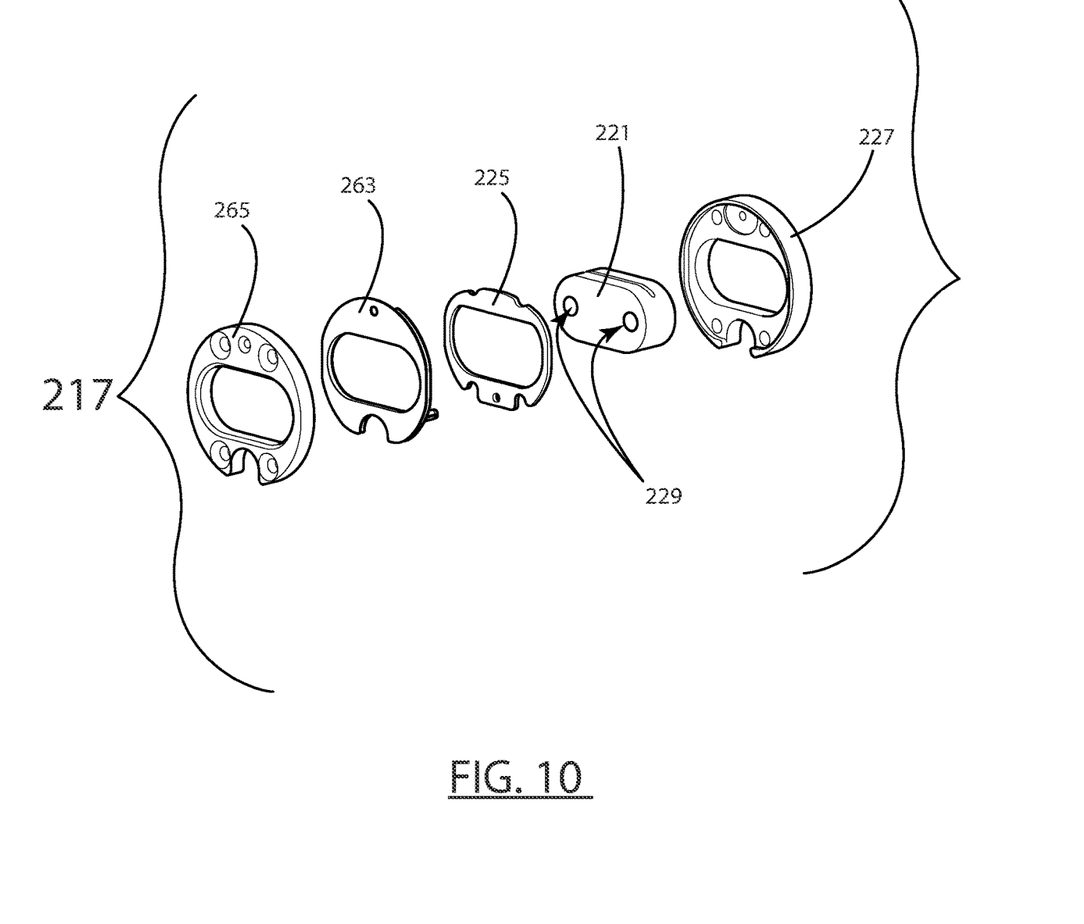
FIG. 10 is an exploded view of a locking block of the iteration of FIG. 9.

FIG. 8 shows a perspective, detail view of an additional manner of engagement between the terminal device as used with a bicycle. A bicycle 158 has a number of frame members. For the purpose of clarity one frame member 160 is shown as it would be engaged with the terminal device 140. The terminal device 140 has a curved lower lip 156 that may be used to engage with a frame member 160 by hooking below the frame member as shown by arrows 161.

One skilled in the art understands that many vehicle frames have tubular frame members. Other vehicle frame-member cross sections are available or may be designed and terminal devices may be designed to accommodate such variations in frame design.

Figure 11:
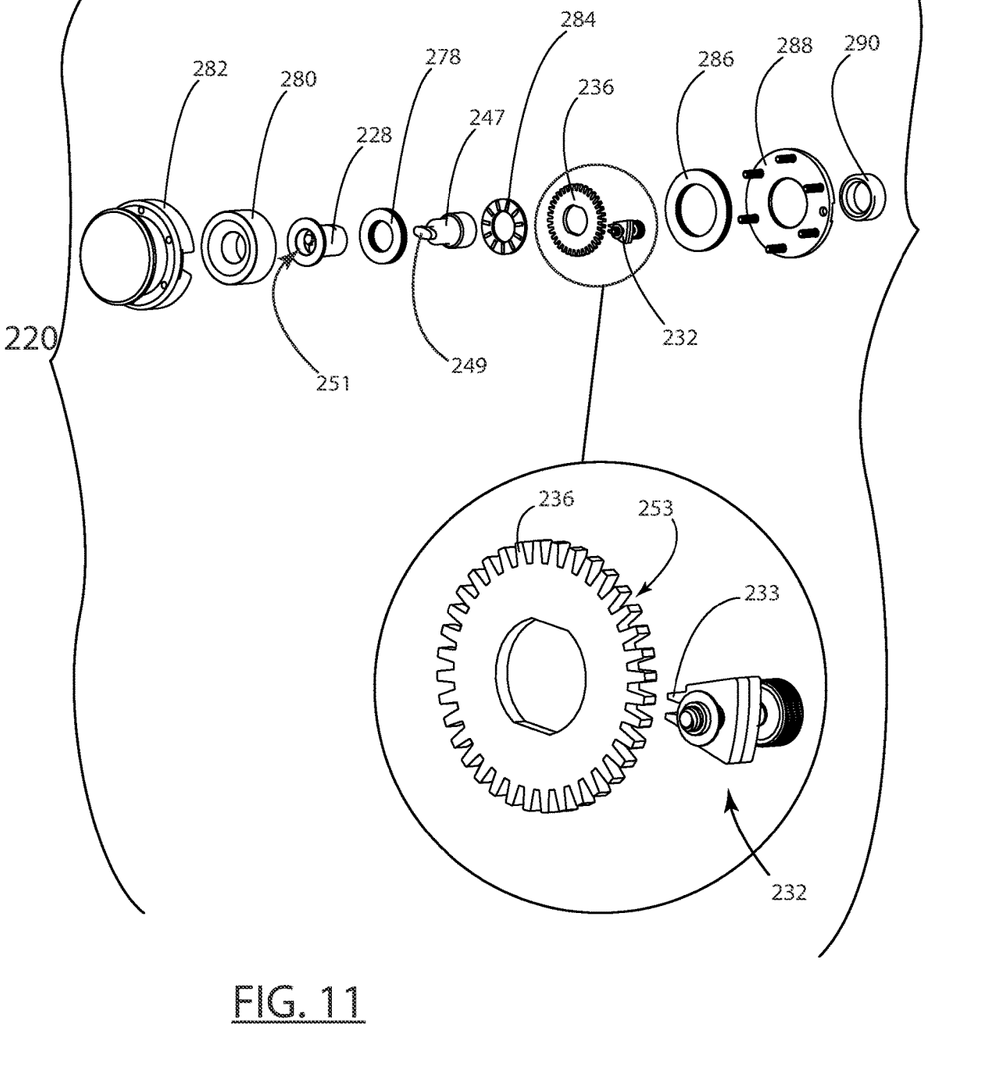
FIG. 11 is an exploded view of a wrist unit of the iteration of FIG. 9.

In FIG. 11, a formed liner 212 fits on the user's forearm and is engaged with distal geometry 237 which is formed to mate with the liner 212 and with embedded connecting hardware such as distal locking mechanism 217. The distal geometry 237 establishes a parallel plane with a distal locking mechanism 217. The locking block 221 (FIG. 12) is fastened to the formed liner 212 and distal geometry 237. The wrist unit assembly 220 and the locking block assembly 217 (except locking block 221) is laminated into a socket 116.

A terminal device 240 allows for secure attachment to and release from a handlebar clamp, similar to receiving member 150 (FIG. 7). The terminal device 240 provides mobility via a 3-axis gimbal with elastomeric dampening on the x-axis by damper 238. One skilled in the art understands that the terminal device 240 is similar to terminal device 140 of FIG. 5.

In FIG. 12, the distal locking mechanism 217 is fastened to a socket 116 and engages the distal geometry 237 (FIG. 11). The locking block 221 is fastened to the distal geometry 237 and penetrates the base plate 265 until retained by locking plate 225. A base plate 265 is chamfered to aid in alignment and insertion of a locking block 221. The locking plate 225 slides on low-friction surfaces within the base plate 265 and pocketed distal cap 227.

The locking block 221 effectively extends the radius and ulna of a human arm and enhances the transfer of pronation/supination from a human limb to the socket, otherwise referred to as distal geometry 237 (FIG. 11). This is accomplished by the pair of alignment holes 229 and the substantially oval shape of the locking block 221. Paired alignment holes engage with the distal geometry 237. The elastic material that makes up the locking block allows movement about the paired alignment holes 229 and therefore paired axis so as to imitate the movement of the ulna radius bones of a forearm.

FIG. 13 illustrates the mechanism of the wrist unit which allows for rotation of the terminal device 240 under load and for indexed, locked rotation of the wrist unit 220 in increments between 5° and 15° and in some embodiments, 10°. An interference mechanism 232 has prongs 233 that engage with teeth 253 of a gear 236 to provide indexed, locked rotation of the wrist unit 220.

A composite spacer 280 transfers radial loads to the housing 282 and provides a surface for bearing combination 278, 284 and 286. A spindle 228 has a through hole 251 that has an interior shape that mates with the end 249 of the adapter 247 in a manner similar to 149 and 151 of the spindle 128 and adapter 147 (FIG. 4). One skilled in the art understands how the adapter 247 engaged with the spindle 228 may rotate freely under a load that is carried by the bearing combination 278, 280, 284 and 286.

A lock-ring 290 threads onto the adapter 247 thus seating the T-hook on the adapter 247 into the mating interior face of the spindle 228. One skilled in the art understands there are various methods of engaging the T-hook into the groove in the spindle such as the depicted threaded collet. A cap 288 closes the housing and provides a bearing surface for bearing 286. The adapter 247 engages with the terminal device 240. In this manner the user may rotate their forearm under load while the terminal device 240 is engaged with a receiving member such as receiving member 150 (FIG. 6). The assembly is contained in housing 282 and covered by cap 288.

These example embodiments should not be construed as limiting. Additions and modifications to what is expressly described herein are included within the scope of the invention. The features of the various embodiments described herein are not mutually exclusive and can exist in various combinations and permutations, even if such combinations or permutations are not made express herein, without departing from the spirit and scope of the invention.

The invention claimed is:

1. A prosthetic hand comprising:
a liner formed to fit on a user's forearm and
a distal cap distal geometry engaged with the formed liner proximal to a distal end of the user's forearm;
said distal geometry removably engaged with a distal locking mechanism;
the distal locking mechanism comprising:
a locking block of a castable elastomeric material, having an oval shape; and
two mounting holes through said oval;
mounting hardware engaging each mounting hole with said distal geometry; wherein
rotation of the liner configured to fit on the user's forearm in a manner similar with respective rotation between ulna and radial bones of the forearm causes rotation of said distal geometry and thus the mounting hardware through the castable elastomeric locking block.

2. The prosthetic hand of claim 1, wherein said locking mechanism is fixedly engaged with a wrist unit assembly; said wrist unit assembly removably engaged with a terminal device; and
said terminal device removably engaged with a receiving unit; wherein
the rotational motion of the liner in the manner similar with respective rotation between the ulna and radial bones is further transferred through said wrist unit and said terminal device and thus to said receiving unit.

3. The prosthetic hand of claim 1, wherein said locking mechanism is fixedly engaged with a wrist unit assembly;
said wrist unit assembly is engaged with a terminal device; and
said terminal device is removably engaged with a receiving unit;
the wrist unit assembly is an apparatus for indexed radial location and rotation under axial load comprising:
a first thrust bearing; and
a second thrust bearing; and
a locking gear; and
a housing containing said wrist unit assembly; and
an interference mechanism configured to lock said locking gear in a radial position;
said first thrust bearing and said second thrust bearing compressed against either side of said locking gear; and
a spindle rotationally engaged with said first thrust bearing; and
an adapter removably engaged with said spindle;
said adapter configured to fixedly engage a terminal device; and
a lock-ring fixedly engaged with said adapter and configured to compress said locking gear; wherein
rotational motion of the spindle is possible while the terminal device provides an axial load on the thrust bearings while the radial position of said housing is locked by engaging said interference mechanism with said locking gear.

* * * * *